United States Patent [19]

Barba et al.

[11] 4,128,457

[45] Dec. 5, 1978

[54] PROCESS FOR THE SEPARATION OF BUTADIENE BY PLURAL STAGE EXTRACTIVE DISTILLATION

[75] Inventors: Diego Barba; Candido D'Agostini; Aldo Pasquinelli, all of Rome, Italy

[73] Assignee: Societa' Italiana Resine S.I.R. S.p.A., Milan, Italy

[21] Appl. No.: 776,042

[22] Filed: Mar. 9, 1977

[51] Int. Cl.² ................. B01D 3/40; C07C 7/08
[52] U.S. Cl. .................. 203/29; 203/53; 203/60; 203/74; 203/77; 203/98; 203/DIG. 19; 260/681.5 R
[58] Field of Search ............... 203/74, 77, 81, 60, 203/53, 99, 98, DIG. 19, 29, 42; 260/681.5 R

[56] References Cited

U.S. PATENT DOCUMENTS

| | | | |
|---|---|---|---|
| 3,000,794 | 9/1961 | Tschopp | 260/681.5 R |
| 3,230,157 | 1/1966 | Hill et al. | 260/681.5 R |
| 3,436,438 | 4/1969 | Takao et al. | 260/681.5 R |
| 3,496,070 | 2/1970 | Woerner et al. | 260/681.5 R |
| 3,705,204 | 12/1972 | Horie et al. | 260/681.5 R |
| 3,851,010 | 11/1974 | Rescalli et al. | 260/681.5 R |

*Primary Examiner*—Wilbur L. Bascomb, Jr.
*Attorney, Agent, or Firm*—Sughrue, Rothwell, Mion, Zinn and Macpeak

[57] ABSTRACT

Butadiene is recovered from a hydrocarbon fraction containing it together with butenes and acetylene hydrocarbons by introducing said fraction into a first extractive distillation column, feeding aqueous acetonitrile into said column above the introduction point of said fraction and extracting a vapor stream containing butadiene below said introduction point; feeding said vapor stream into a second extractive distillation column, feeding aqueous acetonitrile above the introduction point of said vapor stream and recovering a vapor stream consisting essentially of butadiene at the top of said second column; and rectifying this last vapor stream to recover pure butadiene.

13 Claims, 1 Drawing Figure

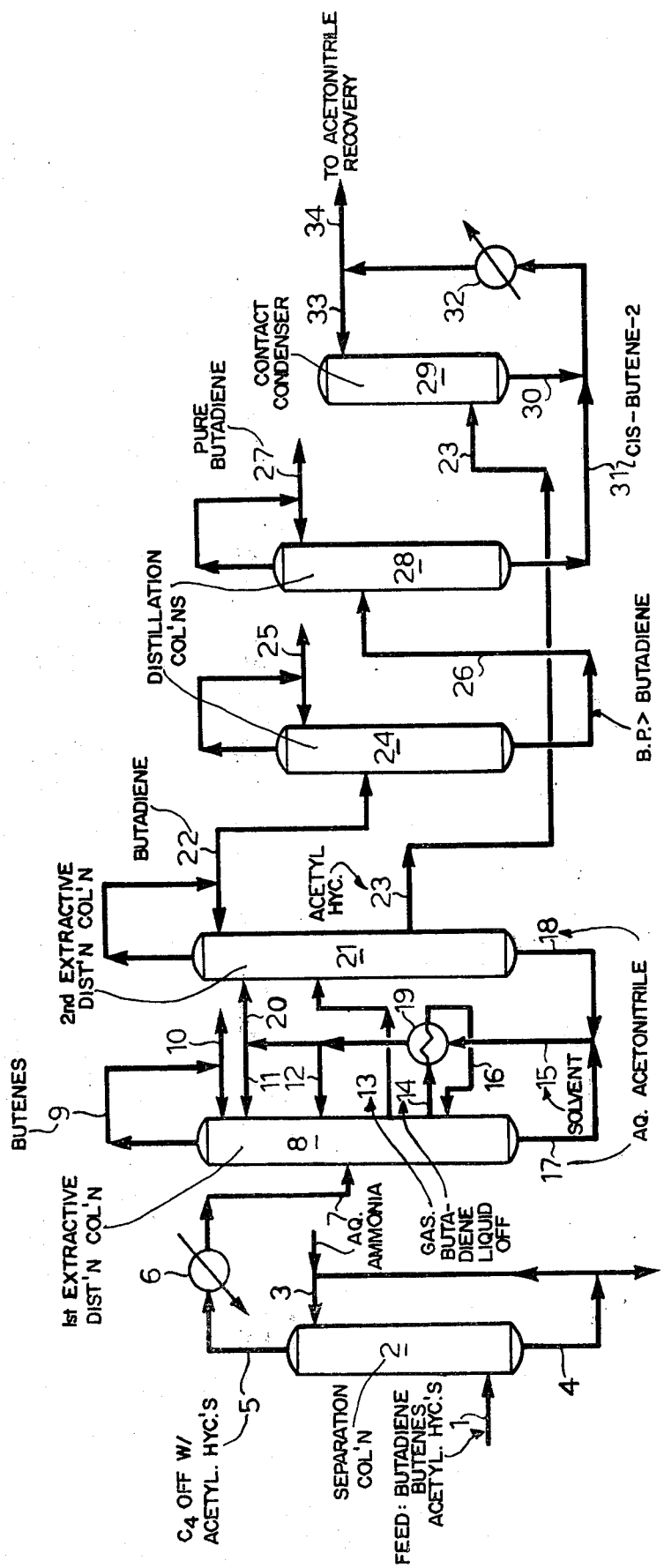

PROCESS FOR THE SEPARATION OF BUTADIENE BY PLURAL STAGE EXTRACTIVE DISTILLATION

The present invention relates to the separation of butadiene (1,3-butadiene) of high purity, from mixtures which contain it together with other hydrocarbons.

The butadiene constitutes a much valued product which finds many applications, particularly in the preparation of synthetic rubber, such as the copolymers of butadiene and styrene or acrylonitrile, and more recently polybutadiene.

The source for butadiene normally used in industry is a hydrocarbon mixture obtained by pyrolysis of petroleum cuts.

In fact, it is known that in the production of ethylene and/or propylene by pyrolysis of liquefied petroleum gas or of naphtha, one obtains, among the secondary products, a fraction ($C_4$ fraction) rich in butadiene and also containing butenes (butene-1, trans-butene-2 and cis-butene-2) and acetylenes (methylacetylene, ethylacetylene and vinylacetylene).

This $C_4$ fraction cannot be fractionated into its individual constituents by means of the normal distillation treatments and, therefore, one resorts to extractive distillation in the presence of special solvents, in order to separate a butadiene having the requisite degree of purity.

In fact, the impurities, especially the acetylenes, have a deleterious effect on the polymerization of butadiene.

The solvents suitable for extractive distillation possess polar characteristics and are normally selected among: acetonitrile, acetone, furfural, dimethylformamide, dioxan, phenol, N-methyl-pyrrolidone and dimethylacetamide.

Operating in accordance with the prior art, it is not easy to obtain high yields of butadiene, especially because of the difficulty in satisfactorily separating this compound from the acetylene hydrocarbons. There are also risks of polymerization of the butadiene, and such a phenomenon, apart from a decrease in the yield, can give rise to deposits and obstructions in the apparatus.

Amongst the various causes for this, the temperature is of special importance because it favours the formation of polymers and therefore it is essential, although then very difficult, to keep the temperature levels in the column at sufficiently low values, inasmuch as the simple use of butadiene polymerisation inhibitors does not produce satisfactory results.

The crude butadiene which is recovered after the extractive distillation treatment is, as known, subjected to rectification for the purpose of removing the residual impurities.

When one operates by means of the conventional methods, the quantity and the nature of these impurities is generally such as to make the rectification treatment very expensive.

In conclusion, in order to obtain sufficiently pure butadiene, with the known methods, one operates with expensive processes which require a high energy consumption and complex equipments of considerable bulk.

According to the present invention one eliminates the disadvantages of the previously known methods, or at least one greatly reduces them, recovering the butadiene from the $C_4$ fractions, by the technique of extractive distillation with aqueous acetonitrile as a solvent and operating within a rigorous set of conditions.

The present invention provides a process for the separation and recovery of butadiene (1,3-butadiene) from a hydrocarbon mixture containing it, which comprises:

introducing into an extractive distillation column having at least 150 plates, operating at a pressure of 3.5–5.5 atmospheres and at a bottom temperature of 110–140° C. and head temperature of 30–50° C., a stream of vaporized hydrocarbon fraction containing butadiene together with butenes and acetylene hydrocarbons at a point intermediate between the head and the bottom and feeding aqueous acetonitrile at one or more points of the column between the head and the point of introduction of the hydrocarbon fraction; recovering at the head of the column a stream consisting essentially of butenes, recovering at the bottom aqueous acetonitrile and extracting at an intermediate point, situated lower than that of the introduction of the hydrocarbon stream, a vapor stream containing the butadiene;

feeding into a second extractive distillation column, having at least 80 plates and operated at temperatures and pressures in the range of those of the first column, the vapor stream containing butadiene coming from the said first column at a point intermediate between the head and the bottom, feeding aqueous acetonitrile at one or more points situated between the head of the column and the point of introduction of the vapor stream containing butadiene; recovering at the head of the column a stream consisting essentially of butadiene, at the bottom aqueous acetonitrile, while extracting a vapor stream consisting essentially of acetylenes at a point of the column located between the bottom and the feed point of the vapor stream containing butadiene;

subjecting the head product of the second extractive distillation column to rectification to separate the last traces of products with a lower boiling point than butadiene and of those with a higher boiling point.

According to a preferred embodiment of the present invention one draws from the first extractive distillation column a flow of liquid from a point situated below the tapping point of the vapor flow containing the butadiene. The said liquid flow is heated at a temperature of up to 90–100° C. and re-introduced into the column at a point corresponding to the plate immediately below the one where the liquid was drawn.

Operating according to the process of the invention, one recovers butadiene with a yield of the order of 96–98% relative to that contained in the hydrocarbon fraction subjected to the treatment. This butadiene is typically of a purity in excess of 99.5%.

A typical composition of the hydrocarbon fraction subjected to the treatment is as follows:

Butadiene: 30–50% by weight.
Butene-2 (cis and trans): about 10–12% by weight.
Acetylenes (methyl-, ethyl- and vinylacetylene): about 1% by weight.
Butene-1: 40–55% by weight.

The said hydrocarbon fractions also contain carbonyl compounds (aldehydes and ketones, generally in quantities of the order of 400–800 ppm) which it is convenient to eliminate or at least reduce to negligible quantities (less than 50 ppm) by a treatment with aqueous ammonia before the treatment by extractive distillation.

Advantageously, the aqueous acetonitrile fed into the first and second extractive distillation column has a water content of from 3 to 10% by weight, and preferably 5% by weight.

The first extractive distillation column contains usually from 150 to 220 plates, and the second extractive distillation column contains usually from 80 to 105 plates (preferably 95–100 plates).

Generally, the hydrocarbon fraction containing butadiene is fed into the first extractive distillation column at a point between the 45th and 65th plate calculated from the top of the column (preferably the 53rd–55th plate), the aqueous acetonitrile is fed at two points, the first between the 6th and 7th plate, the second between the 40th and 60th plate calculated from the top of the column, and the vapor stream containing butadiene is drawn from a point of the column between the 100th and the 170th plate calculated from the top of the column. The weight ratio of aqueous acetonitrile fed to the first extractive column to the hydrocarbon fraction containing butadiene fed to said first column is generally from 7–8:1 to 12–13:1.

Generally, the vapor stream containing butadiene coming from the first column is fed into the second extractive column at a point between the 40th and 60th plate calculated from the top of the column, the aqueous acetonitrile is fed in at a point situated between the 7th and 8th plate calculated from the top of the column and the vapor stream containing acetylene hydrocarbons (mainly vinylacetylene) is drawn from a point situated between the 65th and the 85th plate from the top (preferably the 75th plate). The weight ratio of the aqueous acetonitrile fed to the second extractive column to the vapor stream containing butadiene fed to said second column is generally from 3:1 to 6:1.

Conveniently, the head product of the second extractive column can be rectified by distillation of said head product in a column containing 40–50 plates, thus to remove, at the head, traces of products having a lower boiling point than butadiene and a further distillation of the resulting bottom product in a second column containing 40–55 plates, thus to recover the butadiene as head product and remove traces of products having a higher boiling point than butadiene as bottom product.

A preferred embodiment of the process of the present invention will now be described with reference to the accompanying drawing. The hydrocarbon fraction containing butadiene, butadiene and acetylene hydrocarbons (called hereinafter $C_4$ fraction for the sake of simplicity) is fed through line 1 to column 2 where it is treated with aqueous ammonia in order to eliminate the carbonyl compounds.

For this purpose one feeds into column 2, through the line 3, an aqueous solution containing from 5 to 20 and preferably from 7 to 13 mg of ammonia per ml of solution.

The feeds are controlled in such a manner that the volumetric ratio between the solution of aqueous ammonia and the $C_4$ fraction is between approximately 1:1 and 2:1. Moreover, in column 2 one operates in the liquid phase, in counter-current, at temperatures from 20° to 40° C. (preferably 30° C.), at a pressure of 8–9 atmospheres and with contact times of from 10 to 30 minutes and in general around 20 minutes.

The carbonyl compounds, essentially acetaldehydes, crotonaldehydes and acetone, react with the ammonia and the reaction products remain dissolved in the liquid phase which is discharged from the column 2 through the line 4. A small quantity of the said liquid phase is drained while the remaining part is brought back to titre and recycled to column 2.

The latter can be a packed column, a sieve plate column, a rotating strip column, or any type of apparatus which allows good contact between two non-miscible liquids.

By means of the treatment described, one discharges through 5 the $C_4$ fraction, containing less than 50 ppm of carbonyl compounds (generally about 10 ppm).

The said fraction is vaporized in the exchanger 6 and is fed through line 7 to the first extractive distillation column 8. To this column one also feeds the acetonitrile solvent containing from 3 to 10% by weight of water and preferably 5% by weight.

The column 8 contains from 150 to 220 plates and the $C_4$ fraction is fed to the column at a point between the 45th end the 65th plate counting from the head, and preferably between the 53rd and 55th plate. In the preferred embodiment, the solvent is fed in at two points of the column, through the lines 11 and 12, the first between the 6th and 7th plate and the second between the 40th and 60th plate calculated from the head of the column. In this embodiment it is convenient to feed about ⅔ of the solvent through the line 11 and about ⅓ through the line 12. Moreover, the feeds are controlled in such a manner that one ensures a weight ratio between the solvent (total) and the $C_4$ fraction, in the range of values from 7–8:1 to 12–13:1.

Moreover, in column 8 one operates at a pressure of 3.5–5.5 atmospheres with a temperature at the bottom equal to 110°–140° C., at the head 30°–50° C. and in the intermediate area 60°–80° C.

Operating in these conditions, at the head of the column, through line 9, one recovers a vapor flow containing practically all the butene-1 and the trans-butene-2 contained in the hydrocarbon charge as well as the greater part of the cis-butene-2 contained in the said charge.

A part of these butenes is refluxed to the column and the distillate is drawn through line 10 and subjected to the treatments for the separation of the acetonitrile and the recovery of the butenes.

Moreover, from column 8 one draws a vapor flow, through the line 13, from a point between the 100th and the 170th plate calculated from the head of the column and preferably from a point around the 150th plate. This vapor stream contains the butadiene, the acetylene hydrocarbons present in the feed $C_4$ fraction and the fraction of cis-butene-2 not eliminated with the other butenes at the head of the column. At the bottom of the column 8, through the line 17, one removes the aqueous acetonitrile free of hydrocarbons.

In this manner one prevents the hydrocarbons from passing through the reboiler of the column where they would be subjected to excessively high temperatures and, moreover, relative to the known techniques, one eliminates the stripping column for the separation of the solvents from the hydrocarbons.

The solvent removed at the bottom of the column 8 is recycled through the lines 15, 11 and 12.

According to a preferred embodiment, one provides a removal of liquid through the line 14, preferably two plates below the point of extraction through 13 of the gaseous side current. This removed liquid stream is heated to 90°–100° C. in the exchanger 19, using as heating fluid the recycle aqueous acetonitrile. Finally, this hot liquid is reintroduced into the column through the line 16 at the level of the plate immediately below the plate of extraction. This embodiment increases the efficiency of the separation of the solvent from the hydrocarbons, and also allows a higher thermal efficiency.

The vapor stream containing the butadiene drawn from the column 8 through the line, 13 is fed in to the extractive distillation column 21, having from 80 to 105 plates (preferably 95-100 plates) at a point between the 40th and the 60th plate downwards from the head. To this column one also feeds the aqueous acetonitrile through the line 20 at a point between the 7th and the 8th plate calculated from the top.

In this column one operates in conditions of temperature, pressure and solvent composition similar to those described for the column 8 and with a feed ratio (by weight) of solvent to hydrocarbons of between 3:1 and 6:1.

In these conditions one recovers at the top of the column 21, through the line 22, the butadiene practically free of vinylacetylene (less than 50 ppm and generally about 10-15 ppm).

Also in this case one provides at a point between the 65th and 85th plate (preferably 75th) a removal through line 23 for the vapour containing the vinylacetylene, as well as small quantities of aqueous solvent and butadiene.

From the bottom of the column 21, through the line 18, one recovers the aqueous acetonitrile which is recycled through the lines 15 and 20. The crude butadiene recovered at the top of the column 21, is fed through the line 22 to the distillation column 24.

In the column 24, containing 40-50 plates, one eliminates at the top the lower boiling point substances, essentially the methylacetylene, through line 25. The bottom product of the column 24 is fed, through the line 26, to the distillation column 28.

In this column, containing 40-50 plates one removes at the top the pure butadiene through the line 27, whilst from the bottom one discharges a product consisting essentially of cis-butene-2 and possibly $C_5$ hydrocarbons.

Still with reference to the accompanying drawing the product removed from the column 21 through the line 23 is sent to the contact condensor 29. Because of the known dangers due to the explosivity of the butadiene-vinylacetylene mixtures, the said condensation is effected by direct contact with the condensate.

In practice the bottom product of the condensor 29, is removed through the line 30 and mixed with the bottom product of the column 28 removed through the line 31. The whole is cooled in the exchanger 32 and partly recycled to the condensor 29 through the line 33.

The condensate is sent through the line 34 to a small liquid-liquid extractor (not shown) to recover the dissolved acetonitrile.

The butenes coming from the head of the column 8 normally contain small amounts of acetonitrile which it is convenient to recover, and therefore, these are sent through the line 10 to a liquid-liquid extraction column (not shown) into which one feeds water as the extraction agent.

To this column one also sends a small quantity of the solvent in the cycle, which is thereby subjected to regeneration. The aqueous phase recovered from the said liquid-liquid extraction column is sent to the solvent reconcentration column, together with the aqueous phase coming from the acetylenes' washer and that which is separated in the reflux accumulators in the columns 8 and 21.

For a better heat recovery, the solvent removed at the bottom of the columns 8 and 21 is used as heating fluid in the reboilers of the columns 24 and 28 and for vaporizing the hydrocarbon $C_4$ fraction in the exchanger 6.

As already mentioned, by means of the process of the present invention one recovers butadiene with yields of the order of 96-98% and with a purity of at least 99.5%.

A typical composition of this butadiene is the following:
Butadiene: 99.60%
Butenes: 0.39%
Acetylene compounds: 50 ppm.

Such a butadiene is therefore useful for the normal purposes for which such a product is intended, including polymerization reactions.

EXAMPLE 1

With reference to the accompanying drawing, one feeds to column 2, through the line 1, a hydrocarbon charge, equivalent to 15000 Kg/hour, of the following composition by weight:
methylacetylene: 0.4%
$C_3$ Hydrocarbons: 0.3%
butene-1 and iso-butene: 48.0%
1,3-butadiene: 40.1%
trans-butene-2: 5.9%
cis-butene-2: 4.5%
vinylacetylene and ethylacetylene: 0.55%
$C_5$ Hydrocarbons: 0.2%
carbonyl compounds: 0.05%

The column 2 through line 3 one feeds an aqueous ammonia solution containing about 10 mg of ammonia for each ml of solution, whilst maintaining a weight ratio between the aqueous ammonia solution and the hydrocarbon charge of 1.8:1.

The column 2 is a column with rotating discs, 16 meters high, diameter of the discs 1.25 meters, subdivided into 40 compartments.

Moreover one operates in counter-current, at a pressure of 8 atmospheres, at a temperature of about 30° C., and one discharges a hydrocarbon mixture containing 12 ppm of carbonyl compounds, which is conveyed through line 5 into the vaporizer 6, and the vapour obtained in this manner is fed to the column 8, through the line 7. The column 8 contains 185 plates and has a diameter of 2.8 meters.

The solvent consisting of acetonitrile containing 5% by weight of water is fed, § through the line 11, and Δ through the line 12, in correspondence with, respectively, the 6th and the 50th plate from the head of the column.

The hydrocarbon charge coming from the line 7 is fed in, in correspondence with the 55th plate downwards from the head of the column, while maintaining during the feed a weight ratio of solvent to hydrocarbon charge equal to 8.5:1. Moreover, one operates at a temperature at the head of the column 8 equal to 42° C., at the bottom 135° C., and at a pressure of 4.2 atmospheres measured at the head of the column.

At the head of the column 8, through the line 10, one recovers at a rate of 8,900 kg/hour a flow containing 1.1% by weight of 1,3 butadiene together with a major amount of butene-1 and iso-butene and a minor amount of trans-and cis-butene-2.

From the column 8, through the line 13, one removes a vapor stream, in correspondence with the 145th plate downwards from the head, consisting essentially of 1,3 butadiene and with a total content of butenes (butene-1, cis-and trans-butene-2) equal to 1.1% by weight. The aqueous acetonitrile solvent recovered at the bottom of the column 8 is recycled through the lines 15, 11 and 12.

The vapor stream containing butadiene, removed through the line 13, is fed to column 21, containing 97 plates and with a diameter of 1.6 meters. The vapor stream containing butadiene is fed in, in correspondence with the 45th plate downwards from the head, while the solvent (acetonitrile with 5% water by weight) is fed in at a level corresponding with the 8th plate, again counting downwards from the head of the column 21.

Furthermore, one maintains during the feed a weight ratio between the solvent and the vapor stream containing the butadiene, equal to 4:1. Moreover, in column 21 one operates at a temperature of 42° C. at the head, 135° C. at the bottom, and at a pressure of 4.2 atmospheres measured at the head.

In these conditions the 99.3% of 1,3 butadiene fed to the column, is recovered through the line 22 and the said 1,3 butadiene has a content of vinylacetylene and ethylacetylene equal to 9 ppm. Through the line 23, in correspondence with the 73rd plate downwards from the head of column 21, one recovers a vapor stream which contains essentially the acetylenes. The aqueous solvent recovered at the bottom of the column 21, through the line 18, is recycled through the lines 15 and 20.

The flow recovered at the top of the column 21 (crude 1,3-butadiene) is fed into the column 24 containing 40 plates and having a diameter of 1 meter, at the level of the 18th plate calculated from the top. In the said column one operates with a reflux ratio equal to 55 and one eliminates the products having a lower boiling point than 1,3 butadiene.

The bottom product of the column 24, removed through the line 26, is fed into the column 28, containing 42 plates and having a diameter of 1.7 meters, at the level of the 13th plate calculated from the top. In this column one operates with a reflux ratio equal to 2.3 and one draws at the head a flow of butadiene having a purity degree of 99.7%, containing 5 ppm of vinylacetylene, 15 ppm of ethylacetylene and methyl-acetylene and 5 ppm of carbonyl compounds.

Moreover, one effects a lateral extraction of liquid from the column 8, as hereinbefore described and likewise, the treatments in the condenser 29 and the exchanger 32 are the same as hereinbefore described.

We claim:

1. A process for the separation and recovery of 1,3-butadiene from a hydrocarbon mixture containing it, which comprises:
    introducing into an extractive distillation column having at least 150 plates, operating at a pressure of 3.5-5.5 atmospheres and at a bottom temperature of 110°-140° C. and head temperature of 30°-50° C., a stream of vaporized hydrocarbon fraction containing butadiene together with butenes and acetylene hydrocarbons at a point intermediate between the head and the bottom and feeding aqueous acetonitrile at one or more points of the columm between the head and the point of introduction of the hydrocarbon fraction; recovering at the head of the column a stream consisting essentially of butenes, recovering at the bottom aqueous acetonitrile and removing at an intermediate point, situated lower than that of the introduction of the hydrocarbon fraction, a vapor stream containing butadiene;
    feeding into a second extractive distillation column, having at least 80 plates and operated at temperatures and pressures in the range of those of the first column, the vapor stream containing butadiene extracted from the said first extractive distillation column, at a point intermediate between the head and the bottom, feeding aqueous acetonitrile at one or more points situated between the head of the second extractivedistillation column and the point of introduction of the vapor stream containing butadiene; recovering at the head of the second extractive distillation column a stream consisting essentially of butadiene, at the bottom aqueous acetonitrile, while removing a vapor stream consisting essentially of acetylene hydrocarbons at a point of the second extractive distillation column located between the bottom and the feed point of the vapor stream containing butadiene;
    subjecting the head product of the second extractive distillation column to rectification in a third distillation column to remove the last traces of products with a lower boiling point than butadiene at the head of said third distillation column and of those with a higher boiling point than butadiene as a bottoms product of said third distillation column.

2. The process of claim 1, in which a liquid side stream is removed from the first extractive distillation column from a point situated below the removal point of the vapor stream containing butadiene, this liquid stream is heated at a temperature up to 90°-100° C. and this heated liquid stream is reintroduced into the first extractive distillation column at a point corresponding to the plate immediately below the one where said liquid side stream is drawn.

3. The process of claim 1, in which the hydrocarbon fraction containing butadiene is subjected to a treatment with aqueous ammonia, before being fed into the first extractive distillation column, in order to bring its content in carbonyl compounds below 50 ppm.

4. The process of claim 1, in which said aqueous acetonitrile fed into the first and second extractive distillation columns has a water content of from 3 to 10% by weight.

5. The process of claim 1, in which the first extractive distillation column contains from 150 to 220 plates, the hydrocarbon fraction containing butadiene is fed in at a point of the first extractive distillation column between the 45th and 65th plate downwards from the head, the aqueous acetonitrile is fed in at two points, the first between the 6th and 7th plate, the second between the 40th and 60th plate downwards from the head, and the gaseous stream containing butadiene is drawn from a point of the column situated between the 100th and the 170th plate downwards from the head.

6. The process of claim 1, in which the weight ratio of aqueous acetonitrile fed to the first extractive column to the hydrocarbon fraction containing butadiene fed to said first extractive distillation column is from 7:1 to 13:1.

7. The process of claim 1, in which the second extractive distillation column contains from 80 to 105 plates, the gaseous stream containing butadiene extracted from the first extractive distillation column is fed in at a point situated between the 40th and 60th plate downwards from the head, the aqueous acetonitrile is fed in at a point situated between the 7th and 8th plate downwards from the head and the gaseous stream containing acetylene hydrocarbons is drawn from a point situated between the 65th and the 85th plate downwards from the head.

8. The process of claim 1 in which the weight ratio of the aqueous acetonitrile fed to the second extractive distillation column to the vapor stream containing butadiene fed to said second extractive distillation column is from 3:1 to 6:1.

9. The process of claim 1, in which the head product of the second extractive distillation column is distilled in a first distillation column containing 40-50 plates, with removal, at the head, of the traces of products having a lower boiling point than butadiene, and the resulting bottom product is then distilled in a second distillation column containing 40-55 plates with recovery of the butadiene at the top of said second distillation column and removal of the traces of products having a higher boiling point than butadiene as bottom product.

10. The process of claim 5, in which the hydrocarbon fraction containing butadiene is fed into the first extractive distillation column at a point of the column between the 53rd and the 55th plate and the vapor stream containing butadiene is drawn from said first extractive distillation column at the level of the 150th plate.

11. The process of claim 1, in which the second extractive distillation column contains from 95 to 100 plates.

12. The process of claim 1, in which the vapor stream containing acetylene hydrocarbons is drawn from the second extractive distillation column at the level of the 75th plate from the top of the column.

13. The process of claim 1, wherein said aqueous acetonitrile is fed at one point situated between the head of the second extractive distillation column and the point of introduction of the vapor stream containing butadiene.

* * * * *